United States Patent
Baudry

(10) Patent No.: US 8,892,274 B2
(45) Date of Patent: Nov. 18, 2014

(54) METHOD AND A DEVICE FOR ADAPTING THE MAN-MACHINE INTERFACE OF AN AIRCRAFT DEPENDING ON THE LEVEL OF THE PILOT'S FUNCTIONAL STATE

(71) Applicant: Eurocopter, Cedex (FR)

(72) Inventor: Jean-Pierre Baudry, Toulon (FR)

(73) Assignee: Airbus Helicopters, Marignane Cedex (FR)

( * ) Notice: Subject to any disclaimer, the term of this patent is extended or adjusted under 35 U.S.C. 154(b) by 27 days.

(21) Appl. No.: 13/803,270

(22) Filed: Mar. 14, 2013

(65) Prior Publication Data

US 2013/0268146 A1 Oct. 10, 2013

(30) Foreign Application Priority Data

Apr. 4, 2012 (FR) .................................. 12 01003

(51) Int. Cl.
| | |
|---|---|
| *G01C 23/00* | (2006.01) |
| *G08B 21/00* | (2006.01) |
| *G06F 3/00* | (2006.01) |
| *B64C 19/00* | (2006.01) |
| *A61B 5/18* | (2006.01) |
| *G06F 3/01* | (2006.01) |

(52) U.S. Cl.
CPC . *B64C 19/00* (2013.01); *A61B 5/18* (2013.01); *G01C 23/00* (2013.01); *G06F 3/011* (2013.01)
USPC ................................ 701/3; 340/945; 715/762

(58) Field of Classification Search
USPC .................. 701/3; 340/945, 963; 715/762
See application file for complete search history.

(56) References Cited

U.S. PATENT DOCUMENTS

| 5,075,881 | A | * | 12/1991 | Blomberg et al. ................. 703/2 |
|---|---|---|---|---|
| H1039 | H | * | 4/1992 | Tripp et al. .............. 128/206.28 |
| 7,145,477 | B1 | * | 12/2006 | McBain ......................... 340/945 |
| 2007/0063854 | A1 | * | 3/2007 | Zhang et al. .................. 340/576 |

(Continued)

FOREIGN PATENT DOCUMENTS

| EP | 0292381 A1 | 11/1988 |
|---|---|---|
| EP | 1975783 A1 | 10/2008 |
| FR | 2888967 A1 | 1/2007 |

OTHER PUBLICATIONS

An Approach to Developing Adaptive Interface Technology for Advanced Airborne Crew Stations. Jeffery D. Cress; Dayton Section Symposium, 1997., The 14th Annual Aess/Ieee Fairborn, OH, USA Apr. 9, 1997, New York, NY, USA, IEEE, US, Jan. 1, 1997, pp. 5-10, XP010226722; ISBN: 978-0-7803-3965-1.

(Continued)

*Primary Examiner* — Thomas G Black
*Assistant Examiner* — Tyler Paige
(74) *Attorney, Agent, or Firm* — Brooks Kushman P.C.

(57) ABSTRACT

A method of adapting a man-machine interface (20) of an aircraft (50) depending on the functional level of a pilot, the method comprising a plurality of successive steps. Firstly, before starting a mission, the characteristics of said mission and the characteristics and the physiological state of said pilot are determined. Thereafter, during said mission, the state of the mission and the current state of said aircraft together with a current behavior of said pilot are determined and a current functional level of said pilot is estimated. Thereafter, said current functional level of said pilot is compared with reference functional levels, and said man-machine interface (20) is then adapted in order to assist said pilot automatically and in optimum manner in making the pilot aware of the situation, in the pilot's decision-making, or in the actions taken by the pilot depending on the pilot's stress state or work load state.

18 Claims, 1 Drawing Sheet

(56) References Cited

U.S. PATENT DOCUMENTS

| | | | | |
|---|---|---|---|---|
| 2008/0276186 A1* | 11/2008 | Feduszczak et al. | | 715/762 |
| 2012/0075119 A1* | 3/2012 | Dorneich et al. | | 340/945 |
| 2012/0075123 A1* | 3/2012 | Keinrath et al. | | 340/963 |
| 2012/0078445 A1* | 3/2012 | Krupansky et al. | | 701/3 |
| 2012/0130563 A1* | 5/2012 | McBain | | 701/3 |
| 2013/0261423 A1* | 10/2013 | Herrala et al. | | 600/393 |
| 2013/0268146 A1* | 10/2013 | Baudry | | 701/3 |

OTHER PUBLICATIONS

Situation Awareness Modeling and Pilot State Estimation for Tactical Cockpit Interfaces; HCI International Conference, San Francisco, CA, Aug. 1, 1997, XP055015781, URL:http://people.brandeis.edu/grinkus/mulgund-rinkus_etal_97_sdpvi.pdf.

Search Report and Written Opinion; Application No. FR 1201003; dated Nov. 29, 2012.

* cited by examiner

METHOD AND A DEVICE FOR ADAPTING THE MAN-MACHINE INTERFACE OF AN AIRCRAFT DEPENDING ON THE LEVEL OF THE PILOT'S FUNCTIONAL STATE

CROSS REFERENCE TO RELATED APPLICATIONS

This application claims priority to French patent application FR 12 01003 filed on Apr. 4, 2012, the content of which is incorporated in its entirety by reference herein.

BACKGROUND OF THE INVENTION (1) Field of the Invention

The present invention lies in the field of man-machine interfaces for aircraft. It relates to a method and to a device for adapting the man-machine interface of an aircraft depending on the level of the pilot's functional state. The method and the device are intended more particularly for rotary wing aircraft.

(2) Description of Related Art

In an aircraft, continuous and both-way exchanges take place between the pilot and the aircraft. The pilot communicates with the aircraft via various flight controls and also via various data input means, such as a keypad, a pointer, e.g. a touch tablet enabling certain parameters to be specified, or various switches. Similarly, the aircraft communicates a large amount of information to the pilot, in particular relating to flight conditions, to parameters of the aircraft, and to the outside environment. By way of example, the information may be communicated visually by means of various screens or directly on the pilot's helmet visor, audibly by issuing an alarm or by using a voice synthesis device, or indeed by the sense of touch, by making use of vibration in one or more of the controls of the aircraft. Furthermore, the aircraft may also take charge of the piloting of the aircraft during certain stages of flight by means of an autopilot.

These elements enabling communication to take place between the pilot and the aircraft are referred together as constituting the man-machine interface, commonly specified using the initials MMI. When the aircraft has a copilot, the MMI also enables communication to take place between the copilot and the aircraft. Nevertheless, the description below is limited to communication between the pilot and the aircraft, it being understood that the pilot could be replaced by the copilot at any time.

Nowadays, such an MMI enables the pilot to be informed by providing the pilot with all of the available information depending on the various stages of flight of the aircraft and/or on flying conditions. However, since the piloting of an aircraft is becoming ever more complex, it is advantageous to be able to provide the required information to the pilot at a time that is appropriate. Nevertheless, although human factors are taken into account when designing an MMI, they are not taken into account during a flight. The list of all the information to be presented and the way in which it is to be presented in real time are independent of any human factors associated with the pilot, such as stress, emotions, and fatigue, for example.

Nevertheless, human factors are at the origin of numerous incidents or accidents that occur in aircraft. It is commonly accepted that pilot error or wrong application of a procedure can often be attributed, in full or in part, to an error made by the pilot. Such pilot error may result from one or more human parameters such as pilot stress, fatigue, emotions, or indeed work load when that becomes excessive.

Finally, such human factors, if they become excessive, and when combined with the complexity of certain stages of flight, can have a harmful influence on the pilot's awareness of the pilot's internal environment, such as managing aircraft controls and information, and also of the pilot's external environment, such as the terrain over which the aircraft is flying, the obstacles that might be encountered, and the weather. This harmful influence can have effects not only on the pertinence of decisions made by the pilot, but also on the actions the pilot performs, in particular on the quality of aircraft maneuvers.

All of the necessary information is delivered to the pilot by the MMI, and it is also via the MMI that the pilot can manage the information. Thus, when human factors become excessive, the pilot is under conditions that are prone to error generation and that can lead to an incident or indeed to an accident.

In particular, nowadays, accidents that can be attributed to pilot human factors constitute more than three-quarters of the accidents involving rotary wing aircraft.

At present, the MMI does not take human factors into account in real time, and more particularly it does not take account of the functional state of the pilot of the aircraft, even though solutions exist for attempting to anticipate them or to limit their consequences.

For example, the MMI has a function that makes it possible to detect and then to correct simple pilot errors, such as departure from a flight path or an information input error, in order to avoid such errors leading to an accident. However, that function does not enable multiple pilot errors to be corrected.

During training to become a pilot, pilot selection also makes it possible to test pilots for their abilities, in particular in terms of tolerating stress and in terms of the work load they can perform. Nevertheless, and in spite of the stress that taking an exam can generate, it is not possible to be certain that the character or the emotionality of pilots might not one day have a harmful effect on performing a particular maneuver or stage of flight.

Furthermore, the regular practice carried out by aircraft pilots, whether in flight or on a simulator, and also the additional training they receive, makes it possible, among other things, for pilots to automate the procedures that should be applied under various flight conditions and to improve their knowledge about various types of aircraft. Nevertheless, such practice and training cannot cover all possible situations exhaustively. Furthermore, the high cost of such practice and training can also limit the extent to which it can be used. In addition, the stress and fatigue encountered while practicing are always less than those that a pilot will encounter in a real situation.

Finally, simulations also make it possible to evaluate the work load to which a pilot can be subjected during various stages of flight in a variety of realistic missions. Nevertheless, an exhaustive list of all possible circumstances that might be encountered by a pilot, as a function of the pilot's level of knowledge and experience, cannot be evaluated with any certainty.

BRIEF DESCRIPTION OF THE INVENTION

Document FR 2 888 967 describes a method and a system for determining an MMI. After defining an MMI, a flight is simulated with the MMI and pilot attitudes are acquired, i.e., for example: the gestures made by the pilot, where the pilot looks, and the pilot's reactions. Thereafter, after analyzing those attitudes, the MMI is confirmed as valid or else adjusted, if necessary. That document thus describes developing an MMI, but not how one should be used.

Document EP 0 292 381 describes a method of preparing a statistical model to determine the work load of the pilot of an aircraft. The method is based on pilots estimating their work load during various flights covering a variety of flight conditions. The method then makes it possible to estimate the work load with which a pilot is confronted as a function of the parameters of a flight.

Document US 2007/0063854 also describes a method of estimating the work load of a vehicle driver. That method analyses a subjective evaluation by the vehicle driver of the work load, together with the data streams from various sensors providing information about the physiological state of the driver, about the state of the vehicle, and about the environment. All of that information can then be processed by using various modeling techniques such as Bayesian networks, and neural networks, for example.

The document "Situation awareness modeling and pilot state estimation for tactical cockpit interfaces" from the HIC International Conference, San Francisco, Calif., August 1997, describes a study that establishes the feasibility of an adaptive interface between a pilot and a vehicle. Such an interface mainly comprises three functions, firstly determining the current tactical situation of the aircraft, then determining the current state of the pilot, and finally adapting the interface between the pilot and the vehicle.

Finally, the document "An approach to developing adaptive interface technology for advanced airborne crew stations", from Daytona Section Symposium, New York, US, Apr. 9, 1997, describes a US Air Force research program concerning an adaptive interface between a pilot and an aircraft. One of the essential points of that study relates to a model serving to determine the state of the pilot depending mainly on three event categories: external event, e.g. relating to the environment of the aircraft; internal event, e.g. relating to the physiological state of the pilot; and pilot behavior events.

In the technological background, note should be taken of document EP 1 975 783, which describes a method and a system for adapting a user interface.

It can thus be seen that, at present, there exist solutions for estimating the work load of an aircraft pilot, for training the pilot for a variety of missions that are to be performed, and also for correcting possible errors that the pilot may make while flying. However, those solutions still do not take human factors into account in real time and they therefore do not adapt to the level of the functional state of the pilot throughout a mission. Furthermore, those solutions do not take account of the initial functional state of the pilot before the mission starts. The term "level of the functional state of the pilot" is used to mean the physical, physiological, and psychological abilities of the pilot taken as a whole, enabling the pilot to perform the tasks required in a manner that is effective or not. Below, the term "functional level" is used to designate more simply the level of the functional state of the pilot.

A pilot's tasks correspond to having awareness of the current situation, and to the decisions that need to be taken and the actions that need to be performed by the pilot during a stage of flight. The tasks may be complex to a greater or lesser extent, such as piloting tasks for landing, or navigation tasks such as inputting the coordinates of a way point. Furthermore, those tasks may be made more difficult for the pilot to accomplish, in particular when acting under severe time constraints.

For example, it may be a question of landing close to obstacles in poor visibility or completely redefining a route as a result of discovering a fuel leak, while also taking account of unfavorable weather conditions.

BRIEF SUMMARY OF THE INVENTION

An object of the present invention is thus to propose a method making it possible automatically and in real time to take this functional level of the pilot into account and, during a flight, to adapt the MMI of the aircraft depending on the functional level of the pilot. This method of adapting the MMI of an aircraft thus seeks not only to anticipate the assistance that needs to be provided to the pilot, but also to optimize that assistance.

The method of adapting an aircraft MMI depending on the functional level of a pilot comprises several successive steps. Firstly, before starting a mission, the characteristics of the mission and the characteristics and the initial physiological state of the pilot are determined. Thereafter, during the mission, the state of advance of the mission and a current state of the aircraft are determined together with a current behavior of the pilot. Thereafter, a current functional level of the pilot is determined. After that, a comparison value is determined as a function of the current functional level of the pilot, and it is compared with at least one reference functional level. Finally, the MMI of the aircraft is adapted as a function of the comparison value and of each reference functional level.

The term "adapting the MMI" is used, for example, to designate modifying the MMI in terms of the way it displays various kinds of available information or else performing actions by means of the autopilot of the aircraft. The purpose of this adaptation is to help, to assist, or indeed to take over from the pilot in the current situation.

In order to be able to determine the current functional level of the pilot, it is preferable to know the characteristics of the mission that is to be performed, in particular the tasks that it includes and the difficulty of those tasks. It is also necessary to know the characteristics of the pilot, in particular the pilot's knowledge and experience relating to those various tasks, and also the reactions the pilot might have faced with those tasks, which reactions are associated with the pilot's character.

Furthermore, it is necessary to know the current behavior of the pilot and any change in that behavior during the mission. The current behavior of the pilot is characterized in particular by the pilot's current physiological state.

The physiological state of the pilot is obtained by various measurements made on the pilot by physiological sensors. Amongst other things, and at all times, these measurements serve to determine the pilot's heart rate, brain activity, breathing rate, pupil dilation, eye movements and blinking, level of transpiration, head movements, changes of facial expression such as smiling or scowling, and muscle tension. The various physiological sensors needed to take these measurements are known and conventionally used for this purpose.

Furthermore, the pilot's physiological state is not constant and may vary from day to day as a function of the pilot's mood, state of health, or outside environment such as ambient temperature. In addition, the measurements taken by the physiological sensors may vary over time, so each physiological sensor must therefore be calibrated regularly.

It is thus necessary to take measurements before each mission begins, while the pilot is at rest, in order to determine the initial physiological state of the pilot: the pilot is considered as being at rest when sitting in the cockpit and not performing any tasks.

Thereafter, the current physiological state of the pilot during the mission is determined using the same physiological sensors. The method of the invention can thus observe any change in the physiological state of the pilot between the pilot's initial physiological state and the pilot's current physiological state, thus making it possible to estimate to some extent any change in pilot behavior.

Furthermore, it is also necessary to know the state of advance of the mission, i.e. the stage of the current flight in which the aircraft is to be found and the current tasks that the pilot is to perform, and also the current state of the aircraft. This current state of the aircraft, which includes both functional parameters of the aircraft, e.g. concerning its engines, and flight parameters such as speed or altitude, is obtained by means of various sensors that are conventionally present in an aircraft.

Thus, the principle of the invention relies on different kinds of input data, concerning characteristics that are constant and determined once and forever, before a mission, and concerning objective measurements performed before the mission concerning the initial physiological state of the pilot, and during the mission concerning the current physiological state of the pilot, the state of advance of the mission, and the current state of the aircraft.

Consequently, a current functional level of the pilot is determined during a mission while taking account of these various kinds of input data.

In order to perform these calculations, it is possible to use a technique derived from artificial intelligence, such as learning neural systems. By way of example, such a technique uses evaluations made by pilots during earlier simulation or flights, concerning their current functional levels as a function of various missions and of various flight conditions. An algorithm then makes use of such evaluations together with data from various flight conditions and missions from which the data was obtained, and also the above-mentioned input data in order to obtain an integer value characterizing the current functional level of the pilot.

This calculated current functional level of the pilot corresponds to the ability of the pilot to perform current tasks during the mission as a function of the pilot's experience, knowledge, and character, and also as a function of any change in pilot behavior. This calculation is weighted as a function of the current stage of flight, of the difficulties of the current tasks of the mission, and of the current state of the aircraft.

In this calculation, account may also be taken of the current frequency with which the pilot makes errors as identified by the MMI. By way of example, this error frequency may reveal that the pilot is suffering a high level of stress or a work load that is excessive, thereby characterizing the pilot's current behavior.

A comparison value may then be determined as a function of this current functional level of the pilot and may then be compared with at least one reference functional level. A reference functional level corresponds to a limit functional level beyond which the pilot can no longer be fully aware of the situation or can no longer make appropriate decisions or can no longer perform all of the actions that need to be performed effectively. Help must therefore be given to the pilot in order to enable the mission to continue with a maximum level of safety. This help is then delivered to the pilot by adapting the MMI, at least by presenting appropriate information, and possibly by taking over certain tasks, in part or in full.

This reference functional level is constant regardless of the mission of the aircraft. It is independent of the pilot.

Under such circumstances, the adaptation method is called on to assist or even to take the place of the pilot depending on the comparison value, which is a function of the pilot's current functional level. The invention thus makes it possible in automatic and optimum manner to assist the pilot in making decisions, e.g. as the pilot is working up to a state of being stressed or being subjected to a high work load, or indeed to a state of being completely incapable of coping with the situation.

The characteristics of the mission comprise all of the various flight stages of the mission that is to be performed and the associated tasks, and also the difficulty level of each flight stage and of each task. Any mission can be subdivided into various flight stages, such as takeoff or cruising flight or landing, while also taking account of the environment. For example, a landing on an airfield and a landing on an off-shore oil platform are two distinct flight stages.

Furthermore, each flight stage includes various tasks to be performed, such as piloting, aircraft management, or navigation tasks. Finally, each flight stage and each task must be associated with a difficulty level, with landing on an off-shore oil platform being a priori more complex and thus presenting a greater difficulty level, than landing on an airfield. All of the various associated flight stages and tasks, together with their difficulty levels are drawn up prior to the mission and once and for all. For example they are stored in a first dedicated database.

The mission to be performed must then be subdivided into various flight stages corresponding to stages listed in the database together with associated difficulty levels.

Pilot characteristics comprise the pilot's experience and knowledge enabling the pilot to perform various tasks of the mission, and also the pilot's psychological state. This psychological state, which is directly associated with the pilot's character, corresponds in particular to the reactions a pilot may have when faced with these various tasks, and depending on the pilot's level of stress, for example. It may be established as a result of using appropriate psychological questionnaires in order to determine the dominant traits of the pilot's character, emotionality, and impulsivity, for example.

Furthermore, the pilot's level of experience relates equally well to experience in piloting various types of aircraft and in performing various types of mission, with the pilot's practice of flight stages listed in the first database being incorporated therein.

This psychological state of the pilot and the pilot's knowledge and experience are unlikely to vary rapidly over time, so they are established before a mission. For example they are stored in a second dedicated database. Nevertheless, experience gained on missions in which the pilot is involved may enable this second database to be updated by incorporating the reactions of the pilot so as to add to the pilot's psychological state and experience.

The current behavior of the pilot during the mission comprises the pilot's current physiological state and the pilot's current error frequency. Variation in the pilot's physiological state can be used to estimate some of the change in the pilot's behavior. For example, an increase in the pilot's perspiration or heart rate is a sign of an increase in stress. Similarly, rapid back-and-forth movements of the eyes can also reveal a stress or anxiety situation, and frequent blinking of the eyes may reveal that the pilot is tired. By comparing the pilot's current physiological state with the pilot's initial physiological state, it is possible to determine a change in pilot behavior.

Furthermore, the number of errors committed by the pilot is also a sign that the work load faced by the pilot or the complexity of the tasks to be performed is excessive compared with the pilot's current abilities, e.g. because of major stress or tiredness. The MMI serves to detect and possibly to correct simple errors, such as untimely departures from a flight path to be followed or indeed an error involving inputting parameters lying outside a defined range. Thereafter, by combining the current physiological state of the pilot and the pilot's current error frequency, it is possible to determine whether pilot behavior has changed during the mission.

In an implementation of the invention, the comparison value is determined so as to be equal to the current functional level of the pilot. The method can compare this current functional level of the pilot with each of the reference functional levels, and adapt the MMI accordingly.

Furthermore, it may be advantageous to conserve a history of the pilot's functional levels throughout a mission in order to be able to act in real time to extrapolate the future functional level of the pilot. For this purpose, each current functional level of the pilot is stored in a history of functional levels that constitutes a third dedicated database.

For example, this history is constituted by the successive functional levels of the pilot over the most recent five seconds. This duration of the history may be a function of the flight stage, such as cruising flight or landing, or indeed of flying conditions.

In a preferred implementation of the invention, this history of functional levels is used to calculate a trend for variation in the functional level of the pilot and thereafter a predicted functional level of the pilot is determined. Advantageously, the comparison value is then determined so as to be equal to the predicted functional level of the pilot. Thus, the method may compare this predicted functional level of the pilot with each of the reference functional levels, and respond appropriately and automatically in order to provide the pilot with the best possible assistance in anticipation.

An important originality of the invention lies in the fact that on the basis of a few calculation iterations concerning the current functional level of the pilot, the method is capable of extracting a trend concerning variation in this functional level of the pilot. On the basis of this history, pairs of values ($FLP_i$, $t_i$) are available representing the functional level of the pilot $FLP_i$ at instant $t_i$. Thereafter, it is possible to determine a trend such as a straight line defined by $T=a \times t+b$, that is the closest possible to the set of points ($FLP_i$, $t_i$) on a graph having time $t_i$ plotted along the abscissa axis and functional level $FLP_i$ up the ordinate axis.

This line minimizes the sum of the distances squared between the points ($FLP_i$, $t_i$) and the line, i.e. the function $$F(a, b) = \Sigma_1^n (FLP_i - a \times t_i - b)^2$$

is minimized, where $\underline{n}$ is the number of iterations to take into account and $t_n$ is the time at which the most recent functional level of the pilot $FLP_n$ was determined. This number $\underline{n}$ of iterations depends both on the frequency with which the current functional level of the pilot $FLP_i$ is measured and on the duration to which the history of these functional levels of the pilot $FLP_i$ are stored.

Furthermore, it is possible to define a pair of mean values ($NFP_{mean}, t_{mean}$) over the time intervals $t_1$ to $t_n$, such that:

$$FLP_{mean} = \frac{\sum_{i=1}^{n} FLP_i}{n}$$

and $$t_{mean} = \frac{\sum_{i=1}^{n} t_i}{n}$$

The straight line necessarily passes through the pair ($NFP_{mean}, t_{mean}$). As a result $NFP_{mean} = a \times t_{mean} + b$.

It can thus be deduced that $b = FLP_{mean} - a \times t_{mean}$.

Thereafter, the gradient of the line corresponding to the trend of the pilot's functional level is given by:

$$a = \frac{\sum_{i=1}^{n} [(t_i - t_{mean}) \times (FLP_i - FLP_{mean})]}{\sum_{i=1}^{n} (t_i - t_{mean})^2}$$

Once the trend of variation in the pilot's functional level has been defined, it is possible to estimate a predicted functional level of the pilot PFLP using the formula:

$$PFLP = a \times (t_n + \Delta t) + b$$

where $\Delta t$ represents time variation from time $t_n$. The value of $\Delta t$ may be of the order of one second to a few seconds.

The MMI of the aircraft includes various systems enabling the pilot to communicate with the aircraft and enabling the aircraft to communicate with the pilot.

For example, in order to enable the aircraft to communicate with the pilot, the MMI may include at least one visual information system, such as a screen or a pilot helmet visor, at least one audible information system, and at least one tactile information system. Furthermore, the MMI may also include at least one autopilot system for the aircraft that is capable of taking over from the pilot in order to follow a predetermined flight path, or indeed to perform certain maneuvers.

In an implementation of the invention, the adaptation method has three reference functional levels and acts on the MMI of the aircraft as a function of the comparison value and of these three reference functional levels.

Firstly, if the comparison value is less than all three reference functional levels, there is no need to adapt the MMI in any way. Thus, the MMI is not modified and the pilot is fully capable of performing the various current tasks of the current flight stage. The method then starts a new cycle in order to determine a new comparison value.

However, if the comparison value is equal to or greater than a first reference functional level, and less than a second reference functional level, then it is necessary to adapt the MMI in order to improve the pilot's awareness of the situation. Under such circumstances, at least one modification is made to the way in which the information delivered to the pilot is presented. The purpose of this modification is to sensitize the pilot to particular information on which the pilot needs to focus attention. For example, the number, the size, and the shape of the information as delivered to the pilot, whether that information is visual, audible, or tactile, may be modified. The method then begins a new cycle in order to determine a new comparison value.

In addition, if the comparison value is equal to or greater than a second reference functional level and less than a third reference functional level, the MMI needs to be adapted in order to assist the pilot in making decisions. Under such circumstances, a proposed solution to the current problem that needs to be solved is given to the pilot. The purpose is to provide the pilot with a solution to the detected problem, while leaving the pilot in charge of the aircraft in order to apply that solution or any other solution that the pilot might judge to be more appropriate. For example, the MMI screen displays a safe route to be followed in order to reach a landing zone that is appropriate given the occurrence of a major problem such as an engine fire. The method then starts a new cycle in order to determine a new comparison value.

Finally, if the comparison value is equal to or greater than a third reference functional level, it is essential for the authority of the MMI to be adapted in order to take over from the pilot. Under such circumstances, authority over the aircraft is automatically taken over to the detriment of the pilot. Under such circumstances, the pilot appears to be overwhelmed by the situation and to be incapable of finding a solution or even of applying a solution as proposed to the pilot by the MMI. It is thus better for guaranteeing the safety of the aircraft and of people on board to place the aircraft on autopilot or to correct a maneuver endangering such safety. For example, the autopilot of the aircraft is activated automatically in order to put the machine in a safe state such as remaining in hovering flight or following a predetermined flight path. The method then starts a new cycle in order to determine a new comparison value.

The present invention also provides a device for adapting an MMI of an aircraft depending on the functional level of a pilot. Such a device comprises a set of physiological sensors, at least one scrutineer system, at least two databases, and at least one processor unit. The set of physiological sensors measures a physiological state of the pilot, the scrutineer system monitors the actions of the pilot in order to detect possible errors the pilot might make. In addition, a first database contains the characteristics of various missions that might be performed and a second database contains the characteristics of the pilot. Furthermore, the MMI of the aircraft include at least one visual information system, at least one audible information system, at least one tactile information system, or at least one autopilot system for the aircraft.

During a mission, the processor unit makes it possible to determine the current functional level of the pilot by interpreting the characteristics of the mission, the characteristics of the pilot, the initial physiological state of the pilot before starting the mission, the current physiological state of the pilot during the mission, the current frequency with which the pilot is making errors, the state of advance of the mission, and the current state of the aircraft. The current state of the aircraft is obtained by means of various sensors present in the aircraft. The processor unit then determines a comparison value as a function of the current functional level of the pilot and then compares it with at least one reference functional level. Finally, the processor unit acts on the MMI of the aircraft as a function of the comparison value and of each reference functional level.

In an embodiment of this device, the comparison value is equal to the current functional level of the pilot.

In another embodiment of the device, the functional levels of the pilot are stored in a third database present in the aircraft and thus constituting a history of functional levels. The processor unit can then calculate a trend for variation in the functional level of the pilot on the basis of the history, and can then determine a predicted functional level for the pilot. The comparison value is equal to this predicted functional level for the pilot. The above-mentioned formulas make it possible to determine this predicted functional level for the pilot.

The processor unit has three reference functional levels and acts on the MMI of the aircraft in different ways depending on the comparison value and on the three reference functional levels.

If the comparison value is less than the reference functional levels, no adaptation of the MMI is needed. Consequently, no automatic modification is performed on the MMI.

If the comparison value is equal to or greater than a first reference functional level and less than a second reference functional level, the MMI needs to be adapted in order to improve the pilot's awareness of the situation. Under such circumstances, at least one modification is made to the information delivered to the pilot.

If the comparison value is equal to or greater than a second reference functional level and less than a third reference functional level, it is necessary to adapt the MMI in order to assist the pilot in decision-making. Under such circumstances, a solution to the current problem that needs to be solved is proposed to the pilot.

If the comparison value is equal to or greater than a third reference functional level, then it is essential for the MMI to take over authority and act instead of the pilot. Under such circumstances, authority is automatically taken over by the aircraft to the detriment of the pilot.

BRIEF DESCRIPTION OF THE SEVERAL VIEWS OF THE DRAWINGS

The invention and its advantages appear in greater detail from the following description of embodiments given by way of illustration and with reference to the accompanying figures, in which.

DETAILED DESCRIPTION OF THE INVENTION

Elements present in more than one of the figures are given the same references in each of them.

Figure 1:
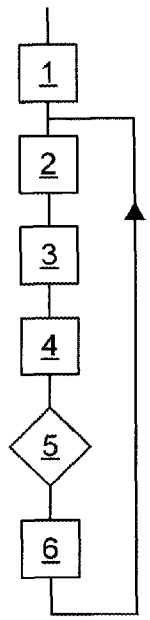
FIG. 1 is a block diagram of the method of the invention.

FIG. 1 is a block diagram of the method of adapting a man-machine interface (MMI) 20 of an aircraft 50 depending on the functional level of a pilot, the method comprising six successive steps.

Before starting a mission, a first step 1 consists in determining the characteristics of the mission and also the characteristics and the initial physiological state of the pilot. Thereafter, while the mission is in progress, a second step 2 consists in determining the state of advance of the mission and a current state of the aircraft 50, together with a current behavior of the pilot. Then, a third step 3 consists in determining a current functional level of the pilot CFLP, and a fourth step 4 consists in determining a comparison value CV as a function of the current function level of the pilot CFLP. A fifth step 5 consists in comparing this comparison value CV with three reference functional values ValRef1, ValRef2, and ValRef3. Finally, a sixth step 6 consists in acting on the MMI 20 of the aircraft 50 as a function of this comparison value CV and of the three reference functional levels ValRef1, ValRef2, and ValRef3.

The reference functional levels ValRef1, ValRef2, and ValRef3 are constants regardless of the mission and of the aircraft. They are determined so that ValRef1 is less than ValRef2, and ValRef2 is less than ValRef3.

Figure 3:
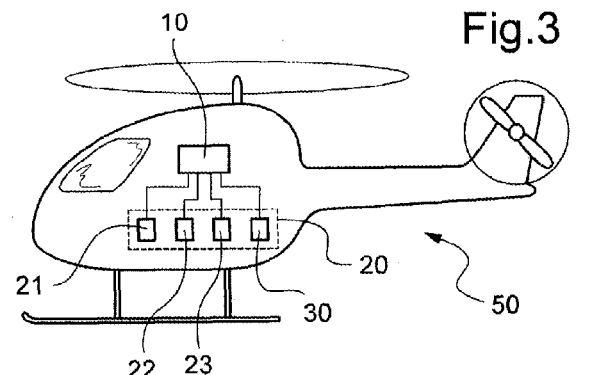
FIGS. 3 and 4 show an embodiment of the device of the invention.
Figure 4:
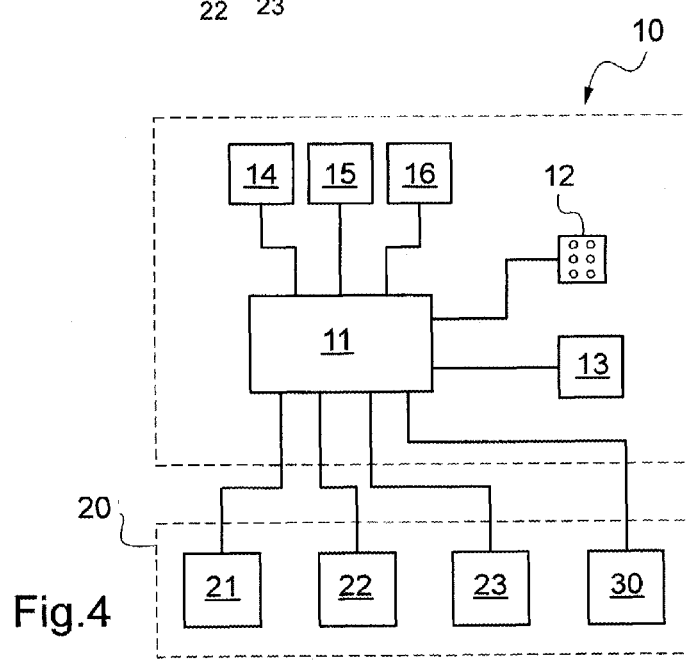

FIGS. 3 and 4 show an embodiment of the device 10 for adapting an MMI 20 installed in an aircraft 50. The device 10 comprises a set of physiological sensors 12, a scrutineer system 13, three databases 14, 15, and 16, and a processor unit 11.

The set of physiological sensors 12 measures a physiological state of the pilot, the scrutineer system 13 monitoring the actions of the pilot in order to detect any errors the pilot might make. Furthermore, a first database 14 contains the characteristics of various potential missions and a second database 15 contains the characteristics of the pilot. In addition, the MMI 20 of the aircraft 50 has a visual information system 21, an audible information system 22, a tactile information system 23, and an autopilot system 30 for the aircraft 50. The third database 16 contains the history of functional levels.

Under such conditions, in the first step 1 of the method of the invention, the mission is split into various flight stages of characteristics that are known and stored in the first database 14. The various tasks that are to be performed during these flight stages and the difficulties associated therewith are thus determined. In addition, the second database contains the characteristics of the pilot, i.e. the pilot's experience, knowledge, and psychological state. Finally, the method makes use of the step of physiological sensors 12 to determine the initial physiological state of the pilot before the mission begins, while the pilot is at rest.

In the second step 2, while the mission is in progress, the state of advance of the mission is determined, i.e. the flight stage in which the aircraft 50 is to be found and a current state of the aircraft 50, i.e. the functional and flight parameters of the aircraft 50. The current state of the aircraft 50 is obtained via various sensors present in the aircraft 50. A current behavior of the pilot is also determined, this behavior comprising the pilot's current physiological state as obtained by the set of physiological sensors 12 and the current frequency with which the pilot is making errors as obtained by the scrutineer system 13.

Then, in the third step 3, the processor unit 11 determines a current functional level of the pilot as a function of the information as determined or measured in the first and second steps 1 and 2. By way of example, the processor unit 11 uses an artificial intelligence model such as learning neural systems enabling all of this information to be interpreted. The current functional level of the pilot as obtained in this way corresponds, in fact, to the ability of the pilot to perform the current tasks of the mission as a function of the pilot's experience, knowledge, and character, and also of the pilot's current behavior, i.e. how the pilot's physiological state is changing and the number of errors being made. This calculation is weighted by the current state of the aircraft 50, the stage of flight, and the difficulties of the current tasks of the mission.

In an implementation of the method, the comparison value CV is determined during the fourth step 4 so as to be equal to the current functional level of the pilot CFLP.

Figure 2:
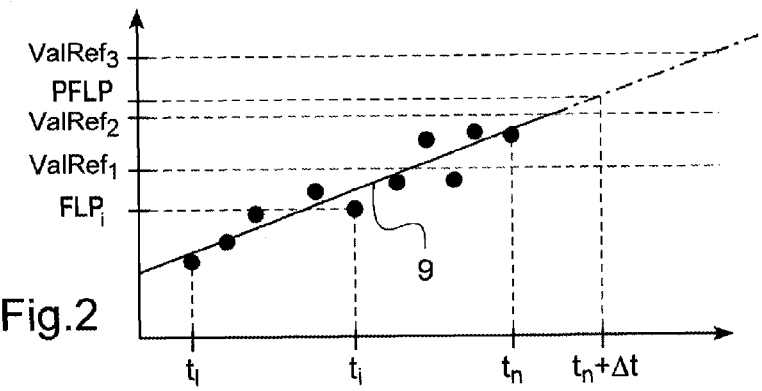
FIG. 2 is a graph showing the functional levels of the pilot of the aircraft.

In a preferred implementation of the method and during the fourth step 4, the on-board computer 11 calculates a trend T for the variation in the functional level of the pilot. This trend T is represented by the graph of FIG. 2, by the straight line 9, where time $\underline{t}$ is plotted along the abscissa axis and the functional level of the pilot FLP is plotted up the ordinate axis. This line 9 is defined so as to be as close as possible to the points $(FLP_i, t_i)$ and corresponds to the equation $T = a \times t + b$.

This line 9 minimizes the sum of the distances squared between these points $(FLP_i, t_i)$ and the line 9. As mentioned above, it can be deduced that:

$$a = \frac{\sum_{i=1}^{n}[(t_i - t_{mean}) \times (FLP_i - FLP_{mean})]}{\sum_{i=1}^{n}(t_i - t_{mean})^2}$$

given that $b = FLP_{mean} - a \times t_{mean}$

Once the trend T of variation in the functional level of the pilot has been defined, it is possible to define a predicted functional level of the pilot PFLP using the formula:

$$PFLP = a \times (t_n + \Delta t) + b$$

with $\Delta t$ representing time variation starting from time $t_n$. The value of $\Delta t$ may be of the order of one second to a few seconds.

Thereafter, a comparison value CV is determined so as to be equal to the predicted functional level of the pilot PFLP.

During the fifth step 5, this comparison value CV is compared with the reference functional levels ValRef1, ValRef2, and ValRef3. These reference functional levels ValRef1, ValRef2, and ValRef3 are shown in the graph of FIG. 2 and they correspond to limit functional levels of the pilot beyond which the pilot can no longer be fully conscious of the situation or can no longer make an appropriate decision or can no longer execute effectively all of the actions needed.

Assistance must then be given to the pilot in order to enable the pilot to continue the mission with maximum safety. This assistance is then delivered by means of the MMI 20 during the sixth stage 6 as a function of the comparison value CV and of the three reference functional levels ValRef1, ValRef2, and ValRef3, at the very least by providing appropriate information, and possibly also by performing certain tasks, in part or in full.

Firstly, if the comparison value CV is less than the reference functional levels, there is no need to adapt the MMI 20. Under such circumstances, no modification is made to the MMI 20, with the pilot being fully capable of performing the various current tasks for the stage of flight. The method then starts a new cycle in order to determine a new comparison value CV.

In contrast, if the comparison value CV is equal to or greater than a first reference functional level ValRef1 and less than a second reference functional level ValRef2, then it is necessary to adapt the MMI 20 in order to improve the pilot's awareness of the situation. Under such circumstances, at least one modification is made to the presentation of the information delivered to the pilot. The method then starts a new cycle in order to determine a new comparison value CV.

Furthermore, if the comparison value CV is equal to or greater than a second reference functional level ValRef2 and less than a third reference functional level ValRef3, it is necessary to adapt the MMI 20 in order to assist the pilot in decision-making. Under such circumstances, a proposed solution to the current problem for solving is shown to the pilot. The method then starts a new cycle in order to determine a new comparison value CV.

Finally, if the comparison value CV is equal to or greater than a third reference functional level ValRef3, it is essential to take over authority MMI 20 in order to act in the place of the pilot. Under such circumstances, the aircraft automatically takes back authority to the detriment of the pilot. The method then starts a new cycle in order to determine a new comparison value CV.

In the example shown in the graph of FIG. 2, it can be seen that the functional level of the pilot FLP at instant $t_n$ lies in the range ValRef1 to ValRef2, and the predicted functional level of the pilot PFLP for instant $t_n + \Delta t$ lies in the range ValRef2 to ValRef3. Thus, in the sixth step 6, the MMI 20 proposes a solution for the current problem to the pilot in order to anticipate this predicted functional level PFLP and assist the pilot in solving the problem.

Naturally, the present invention may be subjected to numerous variations as to its implementation. Although several implementations are described above, it will readily be understood that it is not conceivable to identify exhaustively all possible implementations. It is naturally possible to envisage replacing any of the means described by equivalent means without going beyond the ambit of the present invention.

What is claimed is:

1. A method of adapting a man-machine interface of an aircraft, the method comprising:
   a first step, performed before starting a mission, of determining the characteristics of said mission and the characteristics of said pilot and the pilot's initial physiological state;
   a second step of determining the state of advance of said mission and a current state of said aircraft together with a current behavior of said pilot during said mission;
   a third step of determining a current functional level of said pilot CFLP by using said characteristics of said mission, said characteristics and said initial physiological state of said pilot, said state of advance of said mission, said current state of said aircraft, and said current behavior of said pilot;
   a fourth step of determining a comparison value CV as a function of said current functional level CFLP;
   a fifth step of comparing said comparison value CV with at least one reference functional level ValRef, wherein each reference functional level ValRef is a constant level independent of the pilot; and
   a sixth step of acting on said man-machine interface as a function of the comparison of said comparison value CV with each reference functional level ValRef to thereby adapt said man-machine interface depending on said current functional level of said pilot CFLP.

2. The method according to claim 1, wherein said method has three reference functional levels ValRef1, ValRef2, and ValRef3, such that:
   if said comparison value CV is less than said reference functional levels ValRef1, ValRef2, and ValRef3, no modification of said man-machine is undertaken in said sixth step;
   if said comparison value CV is equal to or greater than a first reference functional level ValRef1 and less than a second reference functional level ValRef2, at least one modification is made to the presentation of information delivered to said pilot in said sixth step;
   if said comparison value CV is equal to or greater than a second reference functional level ValRef2 and less than a third reference functional level ValRef3, a proposed solution to the current problem that is to be solved is given to the pilot during said sixth step; and
   if said comparison value CV is equal to or greater than a third reference functional level ValRef3, said aircraft automatically takes over authority to the detriment of said pilot in said sixth step.

3. The method according to claim 1, wherein said characteristics of said mission comprise a set of various flight stages of said mission and associated tasks, and also a level of difficulty of each flight stage and of each task.

4. The method according to claim 1, wherein said characteristics of said pilot comprise the pilot's level of experience and knowledge in performing various tasks, and also the pilot's psychological state.

5. The method according to claim 1, wherein said current behavior of said pilot during said mission comprises the pilot's current physiological state and a current frequency of pilot errors.

6. The method according to claim 1, wherein said man-machine interface uses learning neural systems in order to determine said current functional level CFLP in said third step.

7. The method according to claim 1, wherein said man-machine interface of said aircraft includes at least one visual information system, at least one audible information system, at least one tactile information system, or at least one autopilot system of said aircraft.

8. The method according to claim 1, wherein said comparison value CV is equal to said current functional level of said pilot CFLP.

9. The method according to claim 1, wherein, in order to determine the comparison value CV, said current functional level CFLP is stored in a history of said functional levels of said pilot FLP, then a trend T is calculated for variations of said functional level FLP on the basis of said history, and then a predicted functional level of said pilot PFLP is determined, said comparison value CV being equal to said predicted functional level PFLP.

10. The method according to claim 1, wherein acting on the man-machine interface as a function of the comparison includes modifying the presentation of information delivered by the man-machine interface to the pilot.

11. The method according to claim 1, wherein acting on the man-machine interface as a function of the comparison includes providing to the pilot via the man-machine interface a proposed solution to a current problem to be solved.

12. A method of adapting a man-machine interface of an aircraft, the method comprising:
   a first step, performed before starting a mission, of determining the characteristics of said mission and the characteristics of said pilot and the pilot's initial physiological state;
   a second step of determining the state of advance of said mission and a current state of said aircraft together with a current behavior of said pilot during said mission;
   a third step of determining a current functional level of said pilot CFLP by using said characteristics of said mission, said characteristics and said initial physiological state of said pilot, said state of advance of said mission, said current state of said aircraft, and said current behavior of said pilot;
   a fourth step of determining a comparison value CV as a function of said current functional level CFLP;
   a fifth step of comparing said comparison value CV with at least one reference functional level ValRef; and
   a sixth step of acting on said man-machine interface as a function of said comparison value CV and of each reference functional level ValRef;
   wherein, in order to determine the comparison value CV, said current functional level CFLP is stored in a history of said functional levels of said pilot FLP, then a trend T is calculated for variations of said functional level FLP on the basis of said history, and then a predicted functional level of said pilot PFLP is determined, said comparison value CV being equal to said predicted functional level PFLP;
   wherein said predicted functional level PFLP is determined using the formula:

$$PFLP = a \times (t_n + \Delta t) + b$$

where $t_n$ represents the time of the most recently determined current functional level $CFLP_n$ and $\Delta t$ represents time variation, the values of $\underline{a}$ and $\underline{b}$ being determined using the following formulae:

$$a = \frac{\sum_{i=1}^{n}[(t_i - t_{mean}) \times (FLP_i - FLP_{mean})]}{\sum_{i=1}^{n}(t_i - t_{mean})^2}$$

$$b = FLP_{mean} - a \times t_{mean},$$

where $FLP_i$ representing said functional level of said pilot corresponding to time $t_i$ $FLP_{mean}$ representing said functional level of said pilot over the time interval $t_1$ to $t_n$, and $t_{mean}$ representing the mean time over said time interval such that $$FLP_{mean} = \frac{\sum_{i=1}^{n} FLP_i}{n}$$

and $$t_{mean} = \frac{\sum_{i=1}^{n} t_i}{n}.$$

13. A device for adapting a man-machine interface of an aircraft, wherein said device comprises:
- a set of physiological sensors measuring a physiological state of said pilot;
- at least one scrutineer system monitoring actions of said pilot in order to detect any errors made by said pilot, thereby determining a pilot error frequency;
- at least two databases, a first database containing characteristics of various potential missions and a second database containing the characteristics of said pilot;
- at least one processor unit comprising at least one memory, at least one processor, and suitable for being connected to said man-machine interface;
- said processor unit including calculation means and storage means, said calculation means executing instructions stored in said storage means for:
- determining before starting a mission, characteristics of said mission taken from said first database and characteristics of said pilot taken from said second database, together with an initial physiological state of said pilot;
- determining the state of advance of said mission and a current stage of said aircraft together with a current behavior of said pilot during said mission, said current behavior of said pilot comprising the pilot's current physiological state and a current pilot error frequency, said current state of said aircraft being obtained by means of various sensors present in said aircraft;
- determining a current functional level of said pilot CFLP making use of said characteristics of said mission, of said pilot's characteristics and initial physiological state, said state of advance of said mission, said current state of said aircraft, and said current behavior of said pilot during said mission;
- determining a comparison value CV as a function of said current functional level CFLP;
- comparing said comparison value CV with at least one reference functional level ValRef, wherein each reference functional level ValRef is a constant level independent of the pilot; and
- acting on said man-machine interface as a function of the comparison of said comparison value CV with said reference functional level ValRef to thereby adapt said man-machine interface depending on said current functional level of said pilot CFLP.

14. The device according to claim 13, said man-machine interface having at least one visual information system, at least one audible information system, at least one tactile information system, or at least one autopilot system of said aircraft, wherein said device includes three reference functional levels ValRef1, ValRef2, and ValRef3, such that:
- said processor unit performs no modification of said man-machine interface when said comparison value CV is less than said reference functional levels ValRef1, ValRef2, and ValRef3;
- said processor unit performs at least one modification in the presentation of information delivered by said man-machine interface to said pilot when said comparison value CV is equal to or greater than a first reference functional level ValRef1 and less than a second reference functional level ValRef2; and
- said processor unit acts via said man-machine interface to propose a solution to said pilot for the current problem that is to be solved when said comparison value CV is equal to or greater than a second reference functional level ValRef2 and less than a third reference functional level ValRef3; and
- said processor unit acts via said man-machine interface automatically to take over authority for said aircraft to the detriment of said pilot when said comparison value CV is equal to or greater than a third reference functional level ValRef3.

15. The device according to claim 13, wherein said comparison value CV is equal to said current functional level CFLP.

16. The device according to claim 13, wherein said functional levels of said pilot are stored in a third database present in said aircraft, thereby constituting a history of said functional levels, and said processor unit determines a predicted functional level of said pilot PFLP, said comparison value CV being equal to said predicted functional level PFLP.

17. The device according to claim 13, wherein the processor unit acts on the man-machine interface as a function of the comparison to modify the presentation of information delivered by the man-machine interface to the pilot.

18. The device according to claim 13, wherein the processor unit acts on the man-machine interface as a function of the comparison to provide to the pilot via the man-machine interface a proposed solution to a current problem to be solved.

* * * * *